United States Patent [19]

Van Doorn et al.

[11] Patent Number: 4,889,956
[45] Date of Patent: Dec. 26, 1989

[54] PREPARATION OF METHOXY PHENYL PHOSPHIDES

[75] Inventors: Johannes A. Van Doorn; Nicolaas Meijboom, both of CM Amsterdam, Netherlands

[73] Assignee: Shell Oil Company, Houston, Tex.

[21] Appl. No.: 175,018

[22] Filed: Mar. 30, 1988

[30] Foreign Application Priority Data

Jun. 22, 1987 [NL] Netherlands ............ 8701449

[51] Int. Cl.$^4$ ............................................. C07F 9/28
[52] U.S. Cl. ..................................................... 568/13
[58] Field of Search ............................ 568/8, 13, 17

[56] References Cited

U.S. PATENT DOCUMENTS 2,437,795  3/1948  Walling ................................. 568/8
4,393,240  7/1983  Stille ..................................... 568/13
4,687,874  8/1987  Oswald et al. ....................... 568/454

OTHER PUBLICATIONS

Inorganic Syntheses, vol. 6, 1975, pp. 155–161, V. D. Blanco et al: Tertiary Phosphines.
Chemistry and Industry, 10/24/70, p. 1378, S. O. Grim et al: A Novel Syntheses of Unsymmetrical Ditertiary Phosphines.
Brown et al., Tetrahedron Letters, vol. 21, pp. 581–584, (1980).

Primary Examiner—John Doll
Assistant Examiner—Stuart L. Hendrickson
Attorney, Agent, or Firm—Dean F. Vance

[57] ABSTRACT

Benzyl- or allyl- di(polar-substituted-phenyl)phosphines are converted in good yield to the corresponding alkali metal di(polar-substituted-phenyl)phosphide by reaction with alkali metal in liquid ammonia.

9 Claims, No Drawings

PREPARATION OF METHOXY PHENYL PHOSPHIDES

FIELD OF THE INVENTION

This invention relates to the production of certain alkali metal di(alkoxyphenyl)phosphides from benzyl- or alkyl-di(alkoxyphenyl)phosphines by reaction of the phosphine with alkali metal in liquid ammonia.

BACKGROUND OF THE INVENTION

The production of arylphosphines can be complicated if all of the substituents on the phosphorus atom are not identical. In situations where the production of mixed alkyl-aryl phosphines is desired, the method of production generally involves the use of at least one organo alkali metal intermediate, the synthesis of which is often difficult or inefficient.

One class of bidentate phosphorus ligands which are mixed alkyl-aryl phosphines has become of interest as a precursor of a catalyst composition useful in the production of a type of polymeric compound known as polyketones or polyketone polymers. These polymers are linear alternating polymers of carbon monoxide and at least one ethylenically unsaturated hydrocarbon. Such polymers have repeatinng units of the formula

wherein B is a moiety of ethylenically unsaturated hydrocarbon polymerized through the ethylenic unsaturation. Such processes for the production of polyketones are illustrated by published European patent application Nos. 0,121,965 and 0,181,014. The processes generally involve the use of a catalyst composition formed from a compound of a Group VIII metal selected from palladium, cobalt or nickel, the anion of a strong non-hydrohalogenic acid and a bidentate ligand containing two Group VA atoms which are preferably phosphorus. Particularly useful as the bidentate phosphorus ligand is the mixed alkyl-aryl phosphine of the formula

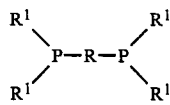

wherein $R^1$ independently is an aryl group and R is a bridging divalent alkylene group, often the trimethylene group. Good results are obtained in the production of polyketones when the phosphine precursor of the catalyst composition is of the above formula wherein each $R^1$ is phenyl and R is trimethylene, i.e., the ligand is 1,3-bis(diphenylphosphino)propane. One of the least complicated methods of producing this ligand is through the reaction of an alkali metal di($R^1$) phosphide, e.g., sodium diphenylphosphide, and an $\alpha,\Omega$-dihaloalkane such as 1,3-dichloropropane. Corresponding methods produce other bis(diarylphosphino)alkanes.

Recent process developments in polyketone production have shown that particularly good results are obtained on occasion of the bidentate ligand has at least one of the aryl groups and preferably each of the aryl groups substituted with a polar group, particularly an alkoxy group, in at least one position ortho or para to the phosphorus. Such bidentate phosphorus ligands are represented by the above formula wherein at least one $R^1$ and preferably each $R^1$ substituent is alkoxyphenyl wherein at least one position of the phenyl ring ortho or para to the phosphorus is substituted with alkoxy. Such diphosphines are produced in a generally preferred procedure by reaction of a dihaloalkane and an alkali metal di(alkoxyphenyl)phosphide wherein each phenyl has the ortho and/or para substitution. The ease and efficiency with which the alkali di(alkoxyphenyl)phosphide is produced, particularly if produced by reaction of alkali metal with the corresponding tri(alkoxyphenyl)phosphine, depends greatly on the location of the alkoxy substituents on the phenyl ring and to some extent the number of alkoxy substituents.

Production of alkali metal diphenylphosphide such as sodium diphenylphosphide by reaction of alkali metal and triphenylphosphine is well known and affords a good yield of phosphide. Such a process also works well with the production of alkali metal di(2-methoxyphenyl)phosphide from reaction of alkali metal and tri(2-methoxyphenyl)phosphine. Reaction of alkali metal and tri(4-methoxyphenyl)phosphine, however, does not give a satisfactory yield of alkali metal di(4-methoxyphenyl)phosphide. See copending U.S. patent application Ser. No. 07/175,021, filed Mar. 30, 1988 (titled Production of Ortho Substituted Dipehnylphosphides) for example. Accordingly, it would be of advantage to provide a process of broader applicability for the production of alkali metal di(alkoxyphenyl)phosphides wherein the phenyl has an alkoxy substituent in at least one of the ring positions ortho or para to the phosphorus.

SUMMARY OF THE INVENTION

This invention relates to an improved process for the production of alkali metal di(alkoxyphenyl)phosphide wherein each phenyl has an alkoxy substituent in at least one of the ring positions ortho or para to the phosphorus. More particularly, the invention relates to a method for the production of such alkali metal phosphides by reaction of alkali metal and the corresponding di(alkoxyphenyl)phosphine, wherein the remaining valence of the phosphorus is satisfied with a benzyl or an allyl group, in liquid ammonia.

DESCRIPTION OF THE INVENTION

The process of the invention comprises the reaction in liquid ammonia of an alkali metal and a benzyl- or allyl-di(alkoxyphenyl)phosphine wherein each phenyl group attached to the phosphorus has an alkoxy substituent in at least one position ortho or para to the phosphorus. Suitable alkali metals are the metals of Group IA of the Periodic Table of Elements, i.e., lithium, sodium, potassium, rubidium and cesium. In part because of economy, the lower alkali metals lithium, sodium and potassium are preferred and best results are obtained when sodium is employed as the alkali metal reactant.

The tertiary di(alkoxyphenyl)phosphine reactants of the process of the invention are tertiary phosphines wherein one valence of the phosphorus is satisfied with a benzyl or an allyl group and the remaining two valences of the phosphorus are satisfied with alkoxyphenyl substituents wherein each phenyl, independently, has an alkoxy substituent in at least one ring position ortho or para to the phosphorus. The alkoxy substituents are alkoxy of up to 10 carbon atoms inclusive, preferably up to 4 carbon atoms inclusive. Such tertiary phosphines are represented by the formula

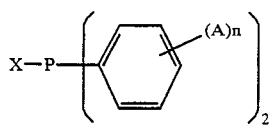

wherein A independently is alkoxy, as defined above, at least one of which is substituted in a ring position ortho or para to the phosphorus in each phenyl ring and n independently is an integer from 1 to 3 inclusive. Illustrative of suitable A groups are methoxy, ethoxy, propoxy, i-propoxy, sec-butoxy, t-butoxy, hexoxy, octoxy and decoxy. Preferred as an A group is a primary straight-chain alkoxy group and particularly preferred is methoxy. The X substituent on the phosphorus is benzyl or allyl, preferably benzyl.

Illustrative of the tertiary phosphine reactant are benzyl-di(2-methoxyphenyl)phosphine, benzyl-(2-methoxyphenyl)(4-ethoxyphenyl)phosphine, benzyl-(2,4-dipropoxyphenyl)(4-ethoxyphenyl)phosphine, allyl-di(2,4,6-trimethoxyphenyl)phosphine, allyl-di(2,6-diethoxyphenyl)phosphine, benzyl-di(2-methoxy-4-hexoxyphenyl)phosphine and benzyl-di(4-methoxyphenyl)phosphine.

The alkali metal and the phosphine reactants are contacted in liquid ammonia. Because ammonia normally boils at −33° C., the reaction mixture must be cooled or alternatively the reaction is conducted under elevated pressure. Although reaction pressures of up to about 4 atmospheres are satisfactory, preferred reaction conditions employ a pressure of substantially one atmosphere and a reaction temperature at which the ammonia is maintained in the liquid phase. Such temperatures are from about −35° C. to about −100° C. but preferably are from about −35° C. to about −80° C. A suitable ratio of alkali metal to the phosphine will vary and typically is from about 1 gram atom of alkali metal to about 3 grams atoms of alkali metal per mol of the phosphine. Best results are obtained when about 2 gram atoms of alkali metal are employed per mole of the phosphine. The quantity of ammonia to be employed is sufficient to maintain the phosphine reactant and the products in solution. Typical amounts of ammonia are from about 1 liter to about 125 liters of ammonia per gram atom of alkali metal, more typically from about 10 liters to about 40 liters of ammonia per gram atom of alkali metal.

Reactants are contacted in reactors where pressure and/or cooling can be employed and where reactant contact can be maintained as by shaking or stirring. No special equipment or materials of construction are required beyond that normally employed in reactions of very active materials such as alkali metals. Subsequent to reaction on acidic material is often added to consume any unreacted alkali metal and the ammonia is removed as by evaporation. The product mixture contains the desired alkali metal di(alkoxyphenyl)phosphide as well as byproducts. The product mixture is separated if desired as by selective extraction but more conventionally is used as such without undue interference by the byproducts. Alternatively, the initial product mixture may be used in a successive reaction without the necessity of removing the ammonia.

The use of a benzyl or allyl di(alkoxyphenyl)phosphine as a starting material results in a good conversion to alkali metal di(alkoxyphenyl)phosphide. Use of other phosphine starting materials such as the tri(alkoxyphenyl)phosphine results in satisfactory yield of desired phosphide in some instances but not in others. The alkali metal phosphide product of the invention is reacted by conventional procedures in liquid ammonia with, for example, 1,3-dibromopropane to give a good yield of 1,3-bis[di(alkoxyphenyl)phosphino]propane, e.g., 1,3-bis[(2-methoxyphenyl)phosphino]propane. Such diphosphines are useful as ligands in the production of polyketone polymers as shown, for example, in copending U.S. patent application Ser. No. 099,263, filed Sept. 21, 1987.

The invention is further illustrated by the following Comparative Examples (not of the invention) and Illustrative Embodiments which should not be construed as limiting.

ILLUSTRATIVE EMBODIMENT I

Sodium di(2-methoxyphenyl)phosphide was produced by the following procedure. To 100 ml of liquid ammonia present in a mechanically stirred reaction vessel maintained at −78° C. with cooling were added successively 8 mmol of sodium and 4 mmol of benzyl-di(2-methoxyphenyl)phosphine. After 4 hours, 4 mmol of ammonia chloride was added to the reaction mixture and after an additional 15 minutes the ammonia was removed by evaporation. Analysis of the residue showed that 89% of the benzyl-di(2-methoxyphenyl)phosphine had been converted to sodium di(2-methoxyphenyl)phosphide.

ILLUSTRATIVE EMBODIMENT II

Sodium di(4-methoxyphenyl)phosphide was produced by substantially the same procedure as that of Illustrative Embodiment I except that benzyl-di(4-methoxyphenyl)phosphine was employed as the starting material in place of the benzyl-di(2-methoxyphenyl)phosphine. Of the benzyl-di(4-methoxyphenyl)phosphine, 89% was found to be converted to sodium di(4-methoxyphenyl)phosphide.

ILLUSTRATIVE EMBODIMENT III

Sodium di(4-methoxyphenyl)phosphide was produced by substantially the same procedure as that of Illustrative I except that allyl-di(4-methoxyphenyl)phosphine was employed as the starting material in place of benzyl-di(2-methoxyphenyl)phosphine. Of the allyl-di(4-methoxyphenyl)phosphine, 99% was converted to sodium di(4-methoxyphenyl)phosphide.

ILLUSTRATIVE EMBODIMENT IV

Sodium di(2,6-dimethoxyphenyl)phosphide was produced by substantially the same procedure as Illustrative Embodiment I except that benzyl-di-(2,6-dimethoxyphenyl)phosphine was employed as the starting material in place of benzyl-di(2-methoxyphenyl)phosphine. Of the benzyl-di(2,6-dimethoxyphenyl)phosphine, 99% was found to be converted to sodium di(2,6-dimethoxyphenyl)phosphide.

ILLUSTRATIVE EMBODIMENT V

Sodium di(2,4,6-trimethoxyphenyl)phosphide was produced by substantially the same procedure as that of Illustrative Embodiment I except that benzyl-di(2,4,6-trimethoxyphenyl)phosphine was employed as the starting material instead of benzyl-di(2-methoxyphenyl)- phosphine. Of the benzyl-di(2,4,6-trimethoxyphenyl)-phosphine, 89% was found to be converted to sodium di(2,4,6-trimethoxyphenyl)phosphide.

If this procedure is repeated utilizing potassium as the alkali metal instead of sodium, a good conversion to potassium di(2,4,6-trimethoxyphenyl)phosphide will be obtained.

COMPARATIVE EXAMPLE I

Sodium di(4-methoxyphenyl)phosphide was produced by substantially the same procedure as that of Illustrative Embodiment I except that tri(4-methoxyphenyl)phosphine was employed as the starting material in place of the benzyl-di(2-methoxyphenyl)phosphine. Of the tri(4-methoxyphenyl)phosphine, 2% was found to be converted to sodium di(4-methoxyphenyl)phosphide.

COMPARATIVE EXAMPLE II

Sodium di(2,6-dimethoxyphenyl)phosphide was produced by substantially the same procedure as that of Illustrative Embodiment I except that tri(2,6-dimethoxyphenyl)phosphine was employed as the starting material in place of benzyl di(2,6-dimethoxyphenyl)phosphine. Of the tri(2,6-dimethoxyphenyl)phosphine, 20% was found to have been converted to sodium di(2,6-dimethoxyphenyl)phosphide.

COMPARATIVE EXAMPLE III

An attempt to produce sodium di(2,4,6-trimethoxyphenyl)phosphide was made by employing a procedure substantially like that of Illustrative Embodiment I except that tri(2,4,6-trimethoxyphenyl)phosphine was employed as starting material in place of the benzyl-di(2-methoxyphenyl)phosphine. There was no apparent conversion of tri(2,4,6-trimethoxyphenyl)phosphine to sodium di(2,4,6-trimethoxyphenyl)phosphide.

COMPARATIVE EXAMPLE IV

The procedure of Illustrative Embodiment I was substantially repeated employing tribenzylphosphine instead of benzyl-di(2-methoxyphenyl)phosphine. There was no apparent conversion of tribenzylphosphine to sodium dibenzylphosphide.

What is claimed is:

1. The process of producing sodium di(methoxyphenyl)phosphide wherein each phenyl has a methoxy substituent in at least one of the ring positions ortho or para to the phosphorus, by reacting sodium metal and the corresponding benzyl- or allyl-di(methoxyphenyl)phosphine, in liquid ammonia.

2. The process of claim 1 wherein the phosphine is represented by the formula

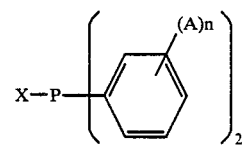

wherein A independently is methoxy substituted in a ring position ortho or para to the phosphorus, n independently is an integer from 1 to 3 inclusive and X is benzyl or allyl.

3. The process of claim 2 wherein X is benzyl.

4. The process of claim 3 wherein n is 1.

5. The process of claim 4 wherein the phosphine is benzyl di(2-methoxyphenyl)phosphine.

6. The process of claim 4 wherein the phosphine is benzyl di(4-methoxyphenyl)phosphine.

7. The process of claim 2 wherein X is allyl.

8. The process of claim 7 wherein the phosphine is allyl-di(4-methoxyphenyl)phosphine.

9. The process of claim 1 wherein said sodium metal and said benzyl- or allyl-di(methoxyphenyl)phosphine are reacted at a pressure of about one atmosphere and a temperature of about −35° C. to about −100° C.

* * * * *